(12) United States Patent
Uchino et al.

(10) Patent No.: US 6,979,434 B2
(45) Date of Patent: *Dec. 27, 2005

(54) METHOD FOR PRODUCING POTASSIUM FLUOROTANTALATE CRYSTAL BEING LOW IN OXYGEN CONTENT AND METHOD FOR PRODUCING POTASSIUM FLUORONIOBATE CRYSTAL BEING LOW IN OXYGEN CONTENT, POTASSIUM FLUOROTANTALATE CRYSTAL BEING LOW IN OXYGEN CONTENT AND POTASSIUM FLUORONIOBATE CRYSTAL

(75) Inventors: Yoshitsugu Uchino, Tokyo (JP); Masanori Kinoshita, Tokyo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 306 days.

This patent is subject to a terminal disclaimer.

(21) Appl. No.: 10/432,398

(22) PCT Filed: Sep. 25, 2002

(86) PCT No.: PCT/JP02/09861

§ 371 (c)(1),
(2), (4) Date: May 21, 2003

(87) PCT Pub. No.: WO03/029147

PCT Pub. Date: Apr. 10, 2003

(65) Prior Publication Data

US 2004/0038415 A1     Feb. 26, 2004

(30) Foreign Application Priority Data

Sep. 27, 2001 (JP) ............................. 2001-296954

(51) Int. Cl.$^7$ ..................... C01G 33/00; C01G 35/00; G01N 1/28; G01N 21/35

(52) U.S. Cl. ...................................... 423/464; 423/463
(58) Field of Search ................................. 423/464, 463

(56) References Cited

U.S. PATENT DOCUMENTS

| | | | | |
|---|---|---|---|---|
| 6,143,571 A | * | 11/2000 | Nuri et al. .................... 436/75 |
| 6,406,512 B2 | * | 6/2002 | Voronenko et al. ........ 75/10.63 |
| 6,764,669 B2 | * | 7/2004 | Isaka et al. .................. 423/464 |
| 6,800,268 B2 | * | 10/2004 | Uchino et al. ............... 423/464 |
| 6,860,941 B2 | * | 3/2005 | Sohama et al. ................ 117/68 |

FOREIGN PATENT DOCUMENTS

| | | |
|---|---|---|
| JP | 49-032897 A | 3/1974 |
| JP | 11-083841 A | 3/1999 |
| JP | 2000-327330 A | 11/2000 |
| WO | WO 2001/047813 A | 7/2001 |

* cited by examiner

Primary Examiner—Ngoc-Yen Nguyen
(74) Attorney, Agent, or Firm—Rothwell, Figg, Ernst & Manbeck, P.C.

(57) ABSTRACT

The object of the present invention is to provide a method of producing low oxygen-containing potassium fluorotantalate crystals or low oxygen-containing potassium fluoroniobate crystals, the crystals obtained by the production method, and a method of analyzing oxygen contained in these crystals.

The method of producing low oxygen-containing potassium fluorotantalate crystals comprises generating recrystallized potassium fluorotantalate crystals by controlled cooling of a saturated solution of potassium fluorotantalate containing hydrofluoric acid as an essential component, collecting the generated recrystallized crystals through filtration, and drying the collected recrystallized crystals in a drying apparatus so as to obtain the crystals, and the production method is characterized in that the saturated solution of potassium fluorotantalate containing hydrofluoric acid as an essential component contains hydrofluoric acid in a concentration of 0.5 mol/l to 10 mol/l.

4 Claims, 1 Drawing Sheet

METHOD FOR PRODUCING POTASSIUM FLUOROTANTALATE CRYSTAL BEING LOW IN OXYGEN CONTENT AND METHOD FOR PRODUCING POTASSIUM FLUORONIOBATE CRYSTAL BEING LOW IN OXYGEN CONTENT, POTASSIUM FLUOROTANTALATE CRYSTAL BEING LOW IN OXYGEN CONTENT AND POTASSIUM FLUORONIOBATE CRYSTAL

TECHNICAL FIELD

The present invention relates to low oxygen-containing potassium fluorotantalate crystals and low oxygen-containing potassium fluoroniobate crystals which contain a low content of oxygen, a method of producing these crystals, and a method of analyzing oxygen which is suitable for analyzing the amount of oxygen contained in these crystals.

BACKGROUND ART

In recent years, tantalum or niobium powders (hereinafter referred to as "metal powders" as their generic name) obtained by reduction of potassium fluorotantalate or potassium fluoroniobate have been increasingly used in the field of capacitors. In order to produce a capacitor with a high performance, metal powders are required to have a high CV value, and therefore various studies have been carried out regarding metal powders.

Potassium fluorotantalate or potassium fluoroniobate is reduced to metal powders, when it is contacted with fumes such as alkaline metal or alkaline earth metal in an atmosphere with inert gas such as argon gas. These metal powders can be used as the electrodes of a capacitor after sintering. However, if potassium fluorotantalate crystals or potassium fluoroniobate crystals which are raw materials for metal powders contain too much oxygen, the amount consumed of alkaline metal or alkaline earth metal which is a reducer in a reduction reaction increases, and further the reduction reaction does not occur uniformly, and thus it is considered that the CV value cannot be improved.

CV value is a value used to express performance regarding the capacitance of a capacitor. The higher the CV value, the smaller capacitor with a larger capacitance can be produced. In recent years, a CV value per weight of metal powders (CV/g) has become large at a level of several ten thousands to several hundred thousands of CV/g, and it is still required to obtain a higher CV value. In order to obtain a higher CV value, it is important to reduce leakage current as well as manufacturing the fine size of metal powders. It is therefore desired to reduce impurities such as metal ions contained in metal powers to a minimum and to produce metal powders containing the lowest level of oxygen.

Nevertheless, tantalum and niobium are metals which have extremely high affinity for oxygen, and it is therefore considered that the reduction of the amount of oxygen contained in potassium fluorotantalate crystals or potassium fluoroniobate crystals would be an extremely difficult technique. Especially, potassium fluorotantalate crystals have a particularly high affinty for oxygen. The amount of oxygen contained in potassium fluorotantalate crystals which have been available on the market is over 3% by weight, and the amount of oxygen contained in potassium fluoroniobate crystals is over 3.5% by weight. The production of these crystals, the oxygen content of which is 2% or less by weight, has been considered to be impossible.

Against this backdrop, as raw materials for metal powders used for a capacitor, low oxygen-containing potassium fluorotantalate crystals or low oxygen-containing potassium fluoroniobate crystals which contain a low level of oxygen before a reduction reaction, have been required.

SUMMARY OF THE INVENTION

Figure 1:
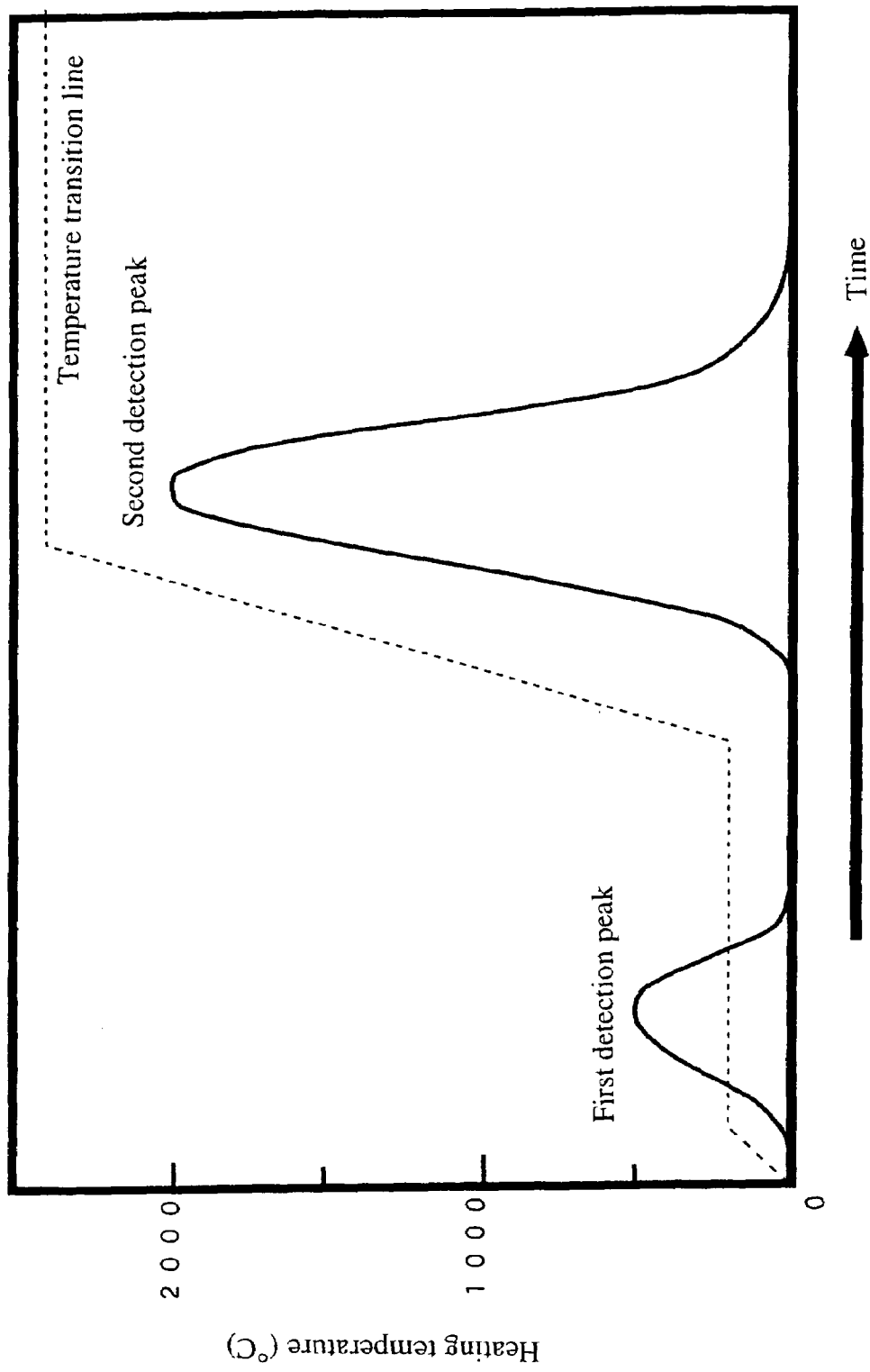
FIG. 1 shows an oxygen detection chart obtained by the method of analyzing oxygen of the present invention.

The present inventors, in their intensive studies, have devised the mother liquor of recrystallized potassium fluorotantalate or recrystallized potassium fluoroniobate obtained in a recrystallization process, have collected the obtained recrystallized crystals through filtration, and have devised a drying process for obtaining the final products, thereby succeeding in reducing the amount of oxygen contained in the products to the lowest level, which has never been achieved before.

A claim relates to a method of producing low oxygen-containing potassium fluorotantalate crystals, which comprises generating recrystallized potassium fluorotantalate crystals by controlled cooling of a saturated potassium fluorotantalate solution comprising hydrofluoric acid as an essential component, collecting the generated recrystallized crystals through filtration, and drying the collected recrystallized crystals in a drying apparatus so as to obtain the crystals; the above method being characterized in that the saturated potassium fluorotantalate solution comprising hydrofluoric acid as an essential component comprises hydrofluoric acid with a concentration of 0.5 mol/l to 10 mol/l. Another claim relates to a production method similar to the above method, that is, a method of producing low oxygen-containing potassium fluoroniobate crystals, which comprises generating recrystallized potassium fluoroniobate crystals by controlled cooling of a saturated potassium fluoroniobate solution comprising hydrofluoric acid as an essential component, collecting the generated recrystallized crystals through filtration, and drying the collected recrystallized crystals in a drying apparatus so as to obtain the crystals; the above method being characterized in that the saturated potassium fluoroniobate solution comprising hydrofluoric acid as an essential component comprises hydrofluoric acid with a concentration of 10 mol/l to 20 mol/l.

Firstly, a background to the development of these production methods will be explained. Oxygen contained in recrystallized potassium fluorotantalate or recrystallized potassium fluoroniobate refers to two types of oxygen such as (1) oxygen derived from water which adsorbs on the surface of crystals or is taken into the crystal grains on the recrystallization stage (hereinbefore and hereinafter referred to as "oxygen derived from water,") and (2) oxygen bound and fixed to the inside of the recrystallized crystal grains (hereinbefore and hereinafter referred to as "bound oxygen.")

The former water is present mainly in a state where it attaches or adsorbs on the surface of crystals, and it is considered that this water is caused by insufficient drying of the crystals, or moisture absorption by the crystals after drying. In contrast, oxygen bound and fixed to the inside of recrystallized crystal grains is present in the form of $K_2TaOF_5$ or $K_3Nb_2OF_{11}$ or the likes. Accordingly, the reduction of the above two types of oxygen should be considered.

The two production methods according to the above described claims are directed towards the reduction of the amount of bound oxygen. In order to achieve this object, it is clearly required to control as much as possible the generation of $K_2TaOF_5$ or $K_3Nb_2OF_{11}$ or the likes existing in recrystallized crystals in the stage of obtaining the recrystallized crystals. The present inventors have studied what component in the above saturated solution has the greatest effect on the control of the generation of the above substances. As a result, they have found that the concentration of hydrofluoric acid in the above saturated solution has the greatest effect. Hydrofluoric acid is an essential component of a saturated solution used to obtain recrystallized potassium fluorotantalate or recrystallized potassium fluoroniobate.

Thus, as a result of intensive studies, the present inventors have found that, if the hydrofluoric acid concentration is set in the range of 0.5 mol/l to 10 mol/l in a saturated potassium fluorotantalate solution and if the concentration is set in the range of 10 mol/l to 20 mol/l in a saturated potassium fluoroniobate solution, bound oxygen can be reduced to the lowest level possible, which is 1% or less by weight. The above described minimum hydrofluoric acid concentrations are required to achieve the minimum concentration of saturated solution in which recrystallization can be carried out for industrial purposes. If the hydrofluoric acid concentration becomes less than the above minimum concentration, oxyfluorides generate and they are mixed in crystals. In contrast, if the hydrofluoric acid concentration exceeds the maximum concentration in each case, a large amount of fine crystals generate, and thereby the amount of water attached to recrystallized potassium fluorotantalate or recrystallized potassium fluoroniobate crystals to be obtained, begins to sharply increase.

Secondly, the present invention relates to "the method of producing low oxygen-containing potassium fluorotantalate crystals, characterized in that the recrystallized crystals are dried while the atmosphere in the drying apparatus is kept at a temperature of 50° C. to 200° C., and that, after the dry process, the recrystallized potassium fluorotantalate crystals are taken out of the drying apparatus into the outside air while the difference between the temperatures of the recrystallized potassium fluorotantalate crystals and the outside air is kept at 50° C. or lower so as to control water adsorption on the recrystallized potassium fluorotantalate crystals." The present invention also relates to "the method of producing low oxygen-containing potassium fluoroniobate crystals, characterized in that the recrystallized crystals are dried while the atmosphere in the drying apparatus is kept at a temperature of 50° C. to 150° C., and that, after the dry process, the recrystallized potassium fluoroniobate crystals are taken out of the drying apparatus into the outside air while the difference between the temperatures of the recrystallized potassium fluoroniobate crystals and the outside air is kept at 50° C. or lower so as to control water adsorption on the recrystallized potassium fluoroniobate crystals."

As stated above, in these production methods, there is disclosed a method of adjusting the hydrofluoric acid concentration of mother liquor so as to reduce the amount of bound oxygen in recrystallized crystals and also reduce oxygen derived from water. In order to reduce the amount of oxygen derived from water, the recrystallized potassium fluorotantalate or recrystallized potassium fluoroniobate which was collected through filtration should be fully dried in the drying process. If only the elimination of water adsorbed on the surface of the recrystallized crystal grains is taken into consideration, the water can easily be eliminated by increasing the drying temperature to the highest possible temperature.

As far as the amount of water adsorbed on the surface of crystals is concerned, the amount of water adsorbed thereon is affected by the grain size of crystals. That is to say, if crystals have the same weight, the smaller the grain size, the larger the specific surface area that can be obtained. The water adsorption site also becomes broader and thereby the amount of water adsorbed increases. Therefore, where the fluctuations in the amount of oxygen derived from water are reviewed, a comparison should be made among recrystallized crystals having almost the same grain size distribution.

However, water is also present in the crystal grains of recrystallized potassium fluorotantalate or recrystallized potassium fluoroniobate. If the elimination of such water is also taken into consideration, water should be eliminated slowly, taking enough time. This is because if drying is carried out at an extremely high temperature, water present in the recrystallized potassium fluorotantalate or the recrystallized potassium fluoroniobate cannot be eliminated, but the dried surface of the recrystallized crystal grains is degenerated. Taking these points into consideration, the present inventors have set the temperature of a dry atmosphere at 200° C. or lower for drying recrystallized potassium fluorotantalate, and at 150° C. or lower for drying recrystallized potassium fluoroniobate.

In the present invention, the drying apparatus has any type of atmosphere including an ambient air atmosphere, a vacuum atmosphere, or an atmosphere substituted by inert gas such as argon gas can be applied, as long as it can efficiently eliminate water contained in recrystallized crystal grains. It is generally considered that a temperature of 100° C. or higher is required to systematically evaporate water in a short time in an ambient air atmosphere. In a vacuum atmosphere or inert gas atmosphere, a lower temperature can be applied. Even in the case of applying a vacuum atmosphere or inert gas atmosphere, high temperature drying can be applied. However, since such high temperature drying significantly increases the production cost, it is not preferable in terms of cost efficiency. Hence, considering industrial productivity, the present inventors have studied appropriate drying temperature in an ambient air atmosphere, and as a result, they have defined 70° C. as the lower limit of drying temperature. If drying is carried out at a temperature of lower than 70° C., drying time is drastically increased, and thereby productivity is significantly decreased. In respect of the structure of the drying apparatus, any drying apparatus can be applied, as long as it has functions in which the readsorption of water removed from recrystallized crystals occurs to the minimum extent possible and the water can be efficiently eliminated outside the drying apparatus.

Problems occurring in the drying process are not limited to the above described one regarding drying temperature. In the case of using powders having hygroscopicity, since the specific surface area of the powders is large, when the powders with a high temperature are cooled to a low temperature in the ambient air, they have water absorption. Accordingly, after the drying process, if recrystallized potassium fluorotantalate or recrystallized potassium fluoroniobate is released to the ambient air while the substance maintains a high temperature, water in the ambient air easily adsorbs on the surface of the recrystallized potassium fluorotantalate or the recrystallized potassium fluoroniobate again. Thus, the present inventors have reviewed this problem, and as a result, they have found that when recrystallized potassium fluorotantalate or recrystallized potassium fluoroniobate is taken out of the drying apparatus after the drying process, if the difference between the temperatures of the substance and the outside air is kept at 50° C. or lower, serious water readsorption on the surface of the substance can be prevented. Against this backdrop, the production method of the present invention has been developed. According to the inventive method, if a drying temperature or cooling method is optimized, drying can be carried out in the ambient air, and low oxygen-containing recrystallized crystals can be obtained without no cost increase.

In view of that the amount of oxygen bound to the conventional recrystallized potassium fluorotantalate is 1.2% or more by weight and the amount of oxygen bound to the conventional recrystallized potassium fluoroniobate is 2.0% or more by weight, the method of the present invention provides recrystallized potassium fluorotantalate or recrystallized potassium fluoroniobate having an extremely reduced amount of oxygen. Therefore, a claim relates to low oxygen-containing potassium fluorotantalate crystals obtained by the present production method, characterized in that the amount of oxygen fixed on the potassium fluorotantalate crystals is 1% or less by weight with respect to the total oxygen comprised in the above crystals. Moreover, another claim relates to low oxygen-containing potassium fluoroniobate crystals obtained by the present production method, characterized in that the amount of oxygen fixed on the potassium fluoroniobate crystals is 1% or less by weight with respect to the total oxygen comprised in the above crystals.

Furthermore, if the production methods according to other claims are used, not only the amount of bound oxygen but the amount of oxygen derived from water is also reduced, so that the total amount of oxygen contained in recrystallized potassium fluorotantalate or recrystallized potassium fluoroniobate can be reduced. Both in the conventional recrystallized potassium fluorotantalate and in the conventional recrystallized potassium fluoroniobate, the amount of oxygen derived from water is approximately 1.5% by weight. However, according to the methods of the present invention, the amount can be reduced to 1.0% or less by weight. Thus, a claim relates to low oxygen-containing potassium fluorotantalate crystals used to produce a capacitor obtained by the present production method, characterized in that the content of oxygen is 2% or less by weight; and another claim relates to low oxygen-containing potassium fluoroniobate crystals used to produce a capacitor obtained by the present production method, characterized in that the content of oxygen is 2% or less by weight.

It has previously been considered that recrystallized potassium fluorotantalate or recrystallized potassium fluoroniobate containing the above-described level of oxygen could not be produced at an industrial level. However, the use of the above described low oxygen-containing potassium fluorotantalate or low oxygen-containing potassium fluoroniobate enables to reduce the consumed amount of alkaline metal or the like, when these substances are reduced to metal powders. Moreover, the use of these substances also enables to carry out a reduction reaction uniformly, and it is therefore expected that the CV value will be significantly improved.

Next, a method of quantifying the amount of oxygen contained in recrystallized potassium fluorotantalate or recrystallized potassium fluoroniobate will be explained. The method of quantifying the amount of oxygen derived from water and the method quantifying the amount of bound oxygen will be explained separately. Water contained in recrystallized crystals is considered to attach or adsorb mainly on the surface of the recrystallized crystal grains. Accordingly, the recrystallized crystals are dried in a drying apparatus which is controlled at a temperature of approximately 110° C. so as to reduce the amount of water contained therein. Thereafter, the value of loss weight is obtained, the amount of water is obtained by conversion of the value of loss weight, and the amount of oxygen derived from water is further obtained by conversion of the amount of water.

It is considered that the amount of bound oxygen is determined by X-ray diffraction for analyzing $K_2TaOF_5$ or $K_3Nb_2OF_{11}$. However, if these substances are not contained in crystals at a rate of several or more % by weight, detection cannot be carried out, giving poor quantitative precision. Therefore, this method has not been used for the quality control of recrystallized potassium fluorotantalate or recrystallized potassium fluoroniobate. That is to say, even if X-ray diffraction was applied to recrystallized potassium fluorotantalate or recrystallized potassium fluoroniobate, this method could not be used to differentiate products which contribute the improvement of performance of a capacitor.

Against this backdrop, the present inventors have developed a method of determining the amount of oxygen derived from water and the amount of bound oxygen separately. Thus, a claim relates to a method of quantifying the amount of oxygen comprised in potassium fluorotantalate crystals or potassium fluoroniobate crystals, characterized in that it comprises placing potassium fluorotantalate crystals or potassium fluoroniobate crystals in a carbon crucible, passing electric current through the above carbon crucible so as to allow the crucible itself to generate heat due to resistance, thereby heating the potassium fluorotantalate crystals or the potassium fluoroniobate crystals placed in the above carbon crucible, extracting oxygen comprised in the above crystals as carbon monoxide, and quantifying the amount of the obtained carbon monoxide so as to quantify the amount of oxygen by the conversion of the amount of the carbon monoxide, the above method being further characterized in that it comprises heating the potassium fluorotantalate crystals or the potassium fluoroniobate crystals placed in the carbon crucible, measuring a first detection peak corresponding to oxygen derived from water within the range of the carbon crucible temperature of 100° C. to 200° C., contacting the oxygen derived from water with a platinum/carbon catalyst which is heated to 1,000° C., and after oxygen which is converted into carbon monoxide for detection is not detected, heating the carbon crucible to a temperature of 2,000° C. or higher, and keeping the carbon crucible at that temperature so as to measure a second detection peak corresponding to bound oxygen.

With reference to FIG. 1, this method of quantifying the amount of oxygen will be explained. That is to say, this oxygen quantification method comprises placing potassium fluorotantalate crystals or potassium fluoroniobate crystals in a carbon crucible, then placing the carbon crucible in a chamber of an oxygen analysis device, and slowly leaking helium gas that is carrier gas into the chamber for atmosphere substitution. This method further comprises passing electric current through the carbon crucible so as to allow the crucible itself to generate heat due to resistance, thereby heating the potassium fluorotantalate crystals or the potassium fluoroniobate crystals placed in the carbon crucible, decomposing the crystals by heating, and eliminating oxygen contained therein as carbon monoxide. This method further comprises quantifying the thus obtained carbon monoxide with a detector and quantifying the amount of oxygen contained in the crystals by conversion of the amount of the obtained carbon monoxide.

In the present invention, while potassium fluorotantalate crystals or potassium fluoroniobate crystals are being heated, oxygen derived from water and bound oxygen are quantified separately as follows. First, in order to quantify only oxygen derived from water, potassium fluorotantalate crystals or potassium fluoroniobate crystals are placed in a carbon crucible and then the temperature of the carbon crucible is raised by resistance heating, thereby heating the crystals placed in the crucible. Thereafter, the first detection peak where the temperature of the carbon crucible is shown in the range of 150° C. to 200° C. is measured. The first detection peak means a peak where oxygen is first detected in FIG. 1, which is first confirmed. This first detection peak can be detected in a low temperature region, and it is considered that this peak corresponds to oxygen derived from water.

After completion of the detection at the first detection peak, the temperature of the carbon crucible is quickly raised to 2,000° C. or higher by heating, and then the carbon crucible is kept at that temperature to detect the second detection peak which corresponds to bound oxygen. It can be said that this second detection peak corresponds to pure bound oxygen because oxygen derived from water is eliminated in advance and potassium fluorotantalate crystals or potassium fluoroniobate crystals which are samples are completely decomposed by heating. According to the above described method, the amount of oxygen derived from water and the amount of bound oxygen can be determined separately.

BEST MODE FOR CARRYING OUT THE INVENTION

Example 1

A solution having a liquid temperature of 70° C., a tantalum concentration of 25 g/l, a potassium concentration of 10 g/l and a hydrofluoric acid concentration of 60 g/l, was used as a saturated potassium fluorotantalate solution. This saturated potassium fluorotantalate solution was poured into a recrystallization bath.

The rate of cooling the above saturated solution was set at 10° C./hour, and the solution was cooled to a liquid temperature of 10° C. so as to obtain recrystallized potassium fluorotantalate. Thereafter, using a filter press, the generated recrystallized potassium fluorotantalate was collected through filtration from the solution after completion of the above recrystallization. The collected recrystallized potassium fluorotantalate was placed in a drying apparatus with an ambient atmosphere and a temperature of 180° C. for the next drying process. After drying for 12 hours, heating is terminated, recrystallized potassium fluorotantalate was cooled to a temperature of 40° C., and then the substance was taken out of the drying apparatus. At the same time, another drying was carried out in the same manner with the exception that the drying atmosphere was substituted by nitrogen gas.

With regard to the grain size distribution of the thus obtained low oxygen-containing potassium fluorotantalate crystals, 80% by weight of crystals had a size of 0.05 mm to 4.00 mm. Where the amount of oxygen contained in this low oxygen-containing potassium fluorotantalate crystals was measured, the content of oxygen was 0.271% by weight (oxygen derived from water was 0.016% by weight and bound oxygen was 0.255% by weight) when drying was carried out in the ambient air atmosphere, and the content of oxygen was 0.054% by weight (oxygen derived from water was 0.009% by weight and bound oxygen was 0.045% by weight) when drying was carried out in an atmosphere substituted by nitrogen. Considering that potassium fluorotantalate which has previously been on the market contained 3% or more by weight of oxygen (oxygen derived from water was 1.5% or more by weight and bound oxygen was 1.2% or more by weight), it is clear that the present potassium fluorotantalate crystals contain an extremely low amount of oxygen.

Analysis of the content of oxygen was carried out as follows. An empty carbon crucible was previously burned at 240° C. in an analyzer (Oxygen/Nitrogen Analyzer (Horiba Ltd., EMGA-620)). To this carbon crucible, 50 mg of low oxygen-containing potassium fluorotantalate crystals was placed as samples. Thereafter, the carbon crucible was heated to a temperature of 200° C. followed by measurement of the first detection peak. Thereafter, the carbon crucible was heated to a temperature of 2,400° C. followed by measurement of the second detection peak. In the meantime, of the oxygen eliminated from low oxygen-containing potassium fluorotantalate, oxygen derived from water was contacted with a platinum/carbon catalyst which was heated to 1,000° C. and it was converted into carbon monoxide. Regarding bound oxygen, oxygen eliminated from low oxygen-containing potassium fluorotantalate by heat decomposition was reacted with carbon constituting the carbon crucible and it was converted into carbon monoxide. Thereafter, each carbon monoxide was quantified using an infrared detector. For calibration of the device, a calibration sample (JCRM RO21, oxygen content ratio: 1.05% by weight) was used. A method of measuring the amount of oxygen contained in low oxygen-containing potassium fluoroniobate, which will be described in the second embodiment, is similar to the above described method.

Example 2

A solution having a liquid temperature of 70° C., a niobium concentration of 40 g/l, a potassium concentration of 50 g/l and a hydrofluoric acid concentration of 300 g/l, was used as a saturated potassium fluoroniobate solution. This saturated potassium fluoroniobate solution was poured into a recrystallization bath.

The rate of cooling the above saturated solution was set at 10° C./hour, and the solution was cooled to a liquid temperature of 10° C. so as to obtain recrystallized potassium fluoroniobate. Thereafter, using a filter press, the generated recrystallized potassium fluoroniobate was collected through filtration from the solution after completion of the above recrystallization.

The collected recrystallized potassium fluoroniobate was placed in a drying apparatus with an ambient air atmosphere and a temperature of 120° C. for the next drying process. After drying for 12 hours, heating is terminated, recrystallized potassium fluoroniobate was cooled to a temperature of 40° C., and then the substance was taken out of the drying apparatus. At the same time, another drying was carried out in the same manner with the exception that the drying atmosphere was substituted by nitrogen gas.

With regard to the grain size distribution of the thus obtained low oxygen-containing potassium fluoroniobate crystals, 85% by weight of crystals had a size of 0.05 mm to 4.00 mm. Where the amount of oxygen contained in this low oxygen-containing potassium fluoroniobate crystals was measured, the content of oxygen was 0.583% by weight (oxygen derived from water was 0.229% by weight and bound oxygen was 0.357% by weight) when drying was carried out in the ambient air atmosphere, and the content of oxygen was 0.382% by weight (oxygen derived from water was 0.111% by weight and bound oxygen was 0.271% by weight) when drying was carried out in an atmosphere substituted by nitrogen. Considering that potassium fluoroniobate which has previously been on the market contained 3.5% or more by weight of oxygen (oxygen derived from water was 1.5% or more by weight and bound oxygen was 2.0% or more by weight), it is clear that the present potassium fluoroniobate crystals contain an extremely low amount of oxygen.

INDUSTRIAL APPLICABILITY

Being different from the conventional production methods, the production method of the present invention can easily produce low oxygen-containing containing potassium fluorotantalate crystals or low oxygen-containing potassium fluoroniobate crystals, which has never been available on the market, without any particular investment in plant and equipment. If these low oxygen-containing potassium fluorotantalate crystals or low oxygen-containing potassium fluoroniobate crystals are used as electrodes of capacitors, electrodes with low leakage current can efficiently be produced, thereby greatly contributing to the stabilization of the quality of capacitors. Moreover, the use of the oxygen analysis method of the present invention enables to analyze oxygen contained in low oxygen-containing potassium fluorotantalate crystals or low oxygen-containing potassium fluoroniobate crystals with high precision, and it can ensure strong quality assurance of the low oxygen-containing potassium fluorotantalate crystals or low oxygen-containing potassium fluoroniobate crystals, when these crystals are provided on the market.

What is claimed is:

1. A method of producing low oxygen-containing potassium fluoroniobate crystals, comprising the steps of recrystallizing potassium fluoroniobate by controlled cooling of a saturated solution of potassium fluoroniobate containing hydrofluoric acid as an essential component, collecting the formed crystals through filtration, and drying the collected crystals in a drying apparatus to obtain a crystals product,
    said method being characterized in that the saturated solution of potassium fluoroniobate containing hydrofluoric acid as an essential component contains hydrofluoric acid in a concentration of 10 mol/l to 20 mol/l.

2. The method of producing low oxygen-containing potassium fluoroniobate crystals according to claim 1, characterized in that in the drying step, the collected crystals are dried in the drying apparatus at an atmospheric temperature of 50° C. to 150° C., followed by a further step of removing the dried crystals from the drying apparatus into the outside air so that a temperature difference between the dried crystals and the outside air is kept at 50° C. or lower to control water adsorption on the removed crystals.

3. Low oxygen-containing potassium fluoroniobate crystals produced by the method according to claim 1, characterized in that the amount of oxygen fixed to the potassium fluoroniobate crystals is, among the total oxygen contained in said crystals, 1% or less by weight with respect to the crystal product.

4. Low oxygen-containing potassium fluoroniobate crystals produced by the method according to claim 2, characterized in that the content of oxygen is 2% or less by weight with respect to the crystal product.

* * * * *